United States Patent
Cho et al.

(10) Patent No.: US 7,026,471 B2
(45) Date of Patent: Apr. 11, 2006

(54) PURIFICATION METHOD OF HYDROXYPROPYLMETHYL CELLULOSE PHTHALATE

(75) Inventors: Kyu-Il Cho, Daejeon (KR); Hyon-Ho Baek, Daejeon (KR)

(73) Assignee: Samsung Fine Chemicals Co., Ltd., Ulsan (KR)

( * ) Notice: Subject to any disclaimer, the term of this patent is extended or adjusted under 35 U.S.C. 154(b) by 141 days.

(21) Appl. No.: 10/475,132

(22) PCT Filed: Apr. 2, 2002

(86) PCT No.: PCT/KR02/00580

§ 371 (c)(1),
(2), (4) Date: Mar. 23, 2004

(87) PCT Pub. No.: WO02/085949

PCT Pub. Date: Oct. 31, 2002

(65) Prior Publication Data

US 2004/0152886 A1    Aug. 5, 2004

(30) Foreign Application Priority Data

Apr. 19, 2001 (KR) ............................... 2001-21076

(51) Int. Cl.
*C07H 1/06*    (2006.01)
*C07H 1/08*    (2006.01)

(52) U.S. Cl. ......................... 536/127; 536/30; 536/32; 536/43; 536/55.3; 536/56; 536/58; 536/66; 536/84; 536/85; 536/87; 536/124

(58) Field of Classification Search .................. 536/30, 536/32, 43, 55.3, 56, 58, 66, 84, 85, 87, 124, 536/127

See application file for complete search history.

(56) References Cited

U.S. PATENT DOCUMENTS 3,629,237 A    12/1971    Koyanagi et al. ........... 260/226
5,047,180 A     9/1991    Steiner et al. ................. 264/5
5,750,148 A *   5/1998    Maruyama et al. ......... 424/494

FOREIGN PATENT DOCUMENTS

CH          160753 A    6/1933

\* cited by examiner

*Primary Examiner*—Patrick Lewis
(74) *Attorney, Agent, or Firm*—Fitzpatrick, Cella, Harper & Scinto

(57) ABSTRACT

The present invention relates to a purification method of hydroxypropylmethyl cellulose phthalate, more particularly to a method of preparing high-purity hydroxypropylmethyl cellulose phthalate through a simple crushing process which comprises: increasing fluidity of reaction product mixture by adding fluidization solvent as a post-treatment process; and spraying it into water through a spray nozzle. As a result, formation of fine granular hydroxypropylmethyl cellulose phthalate particles prevents inter-particle coagulation during the a post-treatment process, and phthalic anhydride reactant, free phthalic acid and remaining acetic acid solvent can be removed effectively.

8 Claims, No Drawings

PURIFICATION METHOD OF HYDROXYPROPYLMETHYL CELLULOSE PHTHALATE

BACKGROUND OF THE INVENTION

FIELD OF THE INVENTION

The present invention relates to a purification method of hydroxypropylmethyl cellulose phthalate and more particularly, to a method of preparing high-purity hydroxypropylmethyl cellulose phthalate through a simple crushing process which comprises: increasing fluidity of reaction product mixture by adding fluidization solvent as a post-treatment process; and spraying it into water through a spray nozzle. As a result, formation of fine granular hydroxypropylmethyl cellulose phthalate particles prevents inter-particle coagulation during the a post-treatment process, and phthalic anhydride reactant, free phthalic acid and remaining acetic acid solvent can be removed effectively.

Generally, cellulose and its derivatives are used for pharmaceuticals, foods, cosmetics and construction additives. Among these, hydroxypropylmethyl cellulose phthalate is used as a filler of enteric coatings, because it is relatively stable in acidic condition.

This hydroxypropylmethyl cellulose phthalate is prepared by esterification of hydroxypropylmethyl cellulose with phthalic anhydride in the presence of sodium acetate in acetic acid solvent to bind phthalic acid to one end of the cellulose molecule. One of such examples is U.S. Pat. No. 3,629,237, which discloses a method of preparing hydroxypropylmethyl cellulose phthalate by mixing hydroxypropylmethyl cellulose having 15–100 cps of viscosity with phthalic anhydride and sodium acetate in acetic acid solvent, carrying out reaction at 80° C. for 5 hr, and making the product mixture as slurry in water.

In this method, it is more important to remove free phthalic acid and residual acetic acid solvent through a suitable post-treatment rather than the synthesis itself, in order to obtain pure granular hydroxypropylmethyl cellulose phthalate. It is because if acetic acid and free phthalic acid are present in the reaction product mixture, it becomes very hard during drying process. As a result, crushing of final product becomes very difficult, and the product may be yellowed or it may smell of acetic acid. Also, when tablets or pellets are coated with a filler, the coating solution is not formed easily due to low solubility and the product stability becomes poor because of decomposition due to acetic acid or free phthalic acid. Therefore, it is essential to entirely remove acetic acid and to reduce free phthalic acid content. Because free phthalic acid can be formed from decomposition of phthalyl group in HPMCP, it is the most important to reduce free phthalic acid content at early stage. Standard for free phthalic acid regulated by pharmacopeias of many countries is less than 1.0%, and most pharmaceutical companies are demanding much lower standard. What is more, because hydroxypropylmethyl cellulose phthalate is an excipient used as filler like enteric coatings, high-purity product with low impurity level is highly required.

In order to effectively remove these impurities, it is required to prevent coagulation of hydroxypropylmethyl cellulose phthalate particles, so that impurities like phthalic acid and acetic acid present between the particles can contact with water and be washed away.

In the conventional preparing method of hydroxypropylmethyl cellulose phthalate, cold water was poured to the reaction product mixture in order to remove the impurities. However, from this method, hydroxypropylmethyl cellulose phthalate in fine powder or granule cannot be obtained because inter-particle coagulation is very severe. This inter-particle coagulation prevents water from penetrating between the particles, so that it becomes difficult to effectively remove phthalic acid and acetic acid. And, additional crushing process is required to obtain granular product.

As described above, the conventional preparing method of hydroxypropylmethyl cellulose phthalate requires a crushing process in order to effectively remove impurities, which is troublesome in practice. Therefore, it is highly required to include this crushing process in a post-treatment method in a natural way.

SUMMARY OF THE INVENTION

In order to solve problems of inter-particle coagulation and difficulty in removing impurities during post-treatment process, a suitable amount of fluidization solvent is added to the reaction product mixture to enhance fluidity of the reaction product mixture. Then, the reaction product mixture having fluidity is sprayed through a spray nozzle into the water to remove the impurities.

Accordingly, an object of the present invention is to provide a preparing method of high-purity hydroxypropylmethyl cellulose phthalate by forming fine-granular particles to prevent inter-particle coagulation and effectively removing free phthalic acid and acetic acid solvent in the product.

DETAILED DESCRIPTION OF THE INVENTION

The present invention is characterized by a purification method of hydroxypropylmethyl cellulose phthalate obtained from the reaction of hydroxypropylmethyl cellulose, alkali acetate, phthalic anhydride and alkali chlorate in acetic acid solvent, wherein 2–4 wt. % of fluidization solvent selected from water or $C_1$–$C_5$ low: alcohol, is added to the reaction product mixture and stirred, the product mixture is sprayed into 10–20 wt. % of water through a spray nozzle whose air or nitrogen gas pressurization speed is 3–8 l/min, and stirring, filtering and drying is performed.

Hereunder is given a more detailed description of the present invention.

The present invention is a new technology of purifying hydroxypropylmethyl cellulose phthalate in high purity for preparing hydroxypropylmethyl cellulose phthalate from low-molecular-weight cellulose or its derivatives, wherein a suitable amount of fluidization solvent is added to the reaction product mixture to enhance fluidity of the reaction product mixture, and it is sprayed into water through a spray nozzle in order to obtain fine-granular particles.

In the present invention, hydroxypropylmethyl cellulose phthalate is prepared through synthesis and purification processes. Hereunder is given a more detailed description of each process.

In the synthesis process, 1 wt. % of hydroxypropylmethyl cellulose is added to 3–6 wt. % of acetic acid solvent and dissolved. Then, after adding 0.4–1 wt. % of alkali acetate, 0.5–1.3 wt. % of phthalic anhydride and 0.01–0.05 wt. % of alkali chlorate, the mixture is stirred slowly at 60–85° C. for 4–6 hr in order to obtain hydroxypropylmethyl cellulose phthalate.

For said hydroxypropylmethyl cellulose, the one whose viscosity in 2%-aqueous solution 3–20 cps and whose chloride content is lower than 0.4% is recommended. For said alkali acetate, sodium acetate or potassium acetate is recommended and, for said alkali chlorate, sodium chlorate or potassium chlorate is recommended.

In the purification process, remaining unreacted phthalic anhydride and phthalic acid and acetic acid solvent are removed. This process is core of the present invention. To the reaction product mixture obtained from the synthesis process, 2–4 wt. % of fluidization solvent (for 1 wt. % of hydroxypropylmethyl cellulose) is added and stirred to enhance fluidity of the reaction product mixture. Then, it is sprayed to 10–20 wt. % of water through a spray nozzle, stirred for 2–10 min, and dried for 4–6 hr at 60–75° C. to obtain high-purity hydroxypropylmethyl cellulose phthalate. In this purification process, hydroxypropylmethyl cellulose phthalate dissolved in acetic acid becomes solid when it contacts with water to form fine granular particles, which prevent inter-particle coagulation of hydroxypropylmethyl cellulose phthalate. As a result, free phthalic acid and acetic acid solvent can be removed effectively. For said fluidization solvent, the one selected from water or $C_1$–$C_5$ low alcohols can be used. For said water, purified water can be used; and for said $C_1$–$C_5$ low alcohols, methanol or ethanol can be used. If the amount of the fluidization solvent is below 2 wt. %, impurities like acetic acid and free phthalic acid may remain in hydroxypropylmethyl cellulose phthalate particles; and if it exceeds 4 wt. %, spraying becomes impossible due to solidification of hydroxypropylmethyl cellulose phthalate. Also, if the amount of water to which the reaction product mixture is sprayed is below 10 wt. %, the high acetic acid concentration in the reaction product mixture renders dissolution of surface particles of the solid hydroxypropylmethyl cellulose phthalate, which causes re-coagulation of the particles. Otherwise, if it exceeds 20 wt. %, a large amount of waste water is generated. For said spray nozzle, the one with 0.5–1.5 mm of internal diameter and whose air or nitrogen gas pressurization speed is 3–8 l/min is recommended. If the internal diameter of the spray nozzle is smaller than 0.5 mm, the productivity becomes poor because only small amount of reaction product mixture can be treated for unit time. Otherwise, if it exceeds 1.5 mm, air or nitrogen gas pressurization speed should be increased. And, if the air or nitrogen gas pressurization speed is below 3 l/min, the particle size is increased and impurities are held between the particles. Otherwise, if it exceeds 8 l/min, an excess amount of nitrogen should be used and hydroxypropylmethyl cellulose phthalate sticks on the reactor wall, so that a large amount of product is lost.

Hydroxypropylmethyl cellulose phthalate obtained from this method contains 30–34% of phthalyl content and only 0.05–0.2% of free phthalic acid. And, particle size of the purified hydroxypropylmethyl cellulose phthalate is 50–300 meshes (300–50 um).

As explained above, the preparing method of purification method of hydroxypropylmethyl cellulose phthalate according to the present invention effectively removes free phthalic acid and reaction solvent remaining in the final product by preventing inter-particle coagulation of hydroxypropylmethyl cellulose phthalate.

The following examples are intended to be illustrative of the present invention and should not be construed as limiting the scope of this invention.

EXAMPLE 1

25 g of hydroxypropylmethyl cellulose (2% aqueous solution; viscosity: 4.25 cps) was added in 100 g of acetic acid solvent and dissolved slowly. When hydroxypropylmethyl cellulose was spread uniformly in acetic acid, 25 g of sodium acetate, 32.5 g of phthalic anhydride and 0.25 g of potassium chlorate were added. After raising temperature to 80–85° C., the mixture was stirred slowly for 5 hr. After the reaction was completed, 100 g of water was added while keeping the temperature at 80–85° C., and the reaction product mixture was stirred for 30 min. After fluidizing the reaction product mixture, it was sprayed into 500 g of water through a spray nozzle. After spraying was completed, the reaction product mixture was stirred for five more minutes, and was filtered with pure water. Then the product was dried for 4–6 hr at 60–75° C. to obtain pure dry granular hydroxypropylmethyl cellulose phthalate.

Analysis of the prepared hydroxypropylmethyl cellulose phthalate according to methods proclaimed in Korean Pharmacopoeia (KP7), United States Pharmacopoeia (USP24) and European Pharmacopoeia (EP348) showed that it contains 33.4% of phthalyl content and only 0.07% of free phthalic acid.

EXAMPLE 2

25 g of hydroxypropylmethyl cellulose (2% aqueous solution; viscosity: 16 cps) was added in 75 g of acetic acid solvent and dissolved slowly. When hydroxypropylmethyl cellulose was spread uniformly in acetic acid, 25 g of sodium acetate, 32.5 g of phthalic anhydride and 0.5 g of potassium chlorate were added. After raising temperature to 80–85° C., the mixture was stirred slowly for 5 hr. After the reaction was completed, 75 g of water was added while keeping the temperature at 80–85° C., and the reaction product mixture was stirred for 30 min. After fluidizing the reaction product mixture, it was sprayed into 500 g of water through a spray nozzle. After spraying was completed, the reaction product mixture was stirred for five more minutes, and was filtered with pure water. Then the product was dried for 4–6 hr at 60–75° C. to obtain pure dry granular hydroxypropylmethyl cellulose phthalate.

Analysis of the prepared hydroxypropylmethyl cellulose phthalate according to methods proclaimed in Korean Pharmacopoeia (KP7), United States Pharmacopoeia (USP24) and European Pharmacopoeia (EP348) showed that it contains 32.7% of phthalyl content and only 0.10% of free phthalic acid.

EXAMPLE 3

25 g of hydroxypropylmethyl cellulose (viscosity: 6.25 cps) was added in 125 g of acetic acid solvent and dissolved slowly. When hydroxypropylmethyl cellulose ether was spread uniformly in acetic acid, 25 g of sodium acetate, 32.5 g of phthalic anhydride and 0.3 g of potassium chlorate were added. After raising temperature to 80–85° C., the mixture was stirred slowly for 5 hr. After the reaction was completed, 50 g of methanol was added while keeping the temperature at 80–85° C., and the reaction product mixture was stirred for 30 min. After fluidizing the reaction product mixture; it was sprayed into 500 g of water through a spray nozzle: After spraying was completed, the reaction product mixture was stirred for five more minutes, and was filtered with pure water. Then the product was dried for 4–6 hr at 60–75° C. to obtain pure dry granular hydroxypropylmethyl cellulose phthalate.

Analysis of the prepared hydroxypropylmethyl cellulose phthalate according to methods proclaimed in Korean Pharmacopoeia (KP7), United States Pharmacopoeia (USP24) and European Pharmacopoeia (EP348) showed that it contains 33.1% of phthalyl content and only 0.12% of free phthalic acid.

EXAMPLE 4

100 g of hydroxypropylmethyl cellulose (viscosity: 13.78 cps) was added in 500 g of acetic acid solvent and dissolved slowly. When hydroxypropylmethyl cellulose ether was spread uniformly in acetic acid, 100 g of sodium acetate, 130 g of phthalic anhydride and 2.5 g of potassium chlorate were added. After raising temperature to 80–85° C., the mixture was stirred slowly for 5 hr. After the reaction was completed, 250 g of water was added while keeping the temperature at 80–85° C., and the reaction product mixture was stirred for 30 min. After fluidizing the reaction product mixture, it was sprayed into 1000 g of water through a spray nozzle. After spraying was completed, the reaction product mixture was stirred for five more minutes, and was filtered with pure water. Then the product was dried for 4–6 hr at 60–75° C. to obtain pure dry granular hydroxypropylmethyl cellulose phthalate.

Analysis of the prepared hydroxypropylmethyl cellulose phthalate according to methods proclaimed in Korean Pharmacopoeia (KP7), United States Pharmacopoeia (USP24) and European Pharmacopoeia (EP348) showed that it contains 33.7% of phthalyl content and only 0.08% of free phthalic acid.

COMPARATIVE EXAMPLE 50 g of hydroxypropylmethyl cellulose (viscosity: 15–100 cps) was added in 200 g of acetic acid solvent and dissolved slowly. When hydroxypropylmethyl cellulose was spread uniformly in acetic acid, 50 g of sodium acetate, 60 g of phthalic anhydride and 5 g of potassium chlorate were added. After raising temperature to 80–85° C., the mixture was stirred slowly for 5 hr. After the reaction was completed, the reaction product mixture was sprayed into 200 g of water. After spraying was completed, the reaction product mixture was stirred for five more minutes, and was filtered with pure water. Then the product was dried for 4–6 hr at 60–75° C. to obtain hydroxypropylmethyl cellulose phthalate.

Analysis of the prepared hydroxypropylmethyl cellulose phthalate showed that it contains 33.2% of phthalyl content. However, it also contained as much as 0.82% of free phthalic acid and 3% of remaining acetic acid.

From these examples, it was confirmed that high-purity hydroxypropylmethyl cellulose phthalate can be obtained by, after synthesizing hydroxypropylmethyl cellulose phthalate, enhancing fluidity of the reaction product mixture with water or low alcohols and spraying it into water through a spray nozzle.

As explained in detail above, the present invention provides a preparing method of high-purity hydroxypropylmethyl cellulose phthalate by reducing particle size through a special spraying method under a specific condition, which prevents inter-particle coagulation of hydroxypropylmethyl cellulose phthalate and effectively removes phthalic acid and acetic acid remaining in the final product.

What is claimed is:

1. A purification method of hydroxypropylmethyl cellulose phthalate from a hydroxypropylmethyl cellulose phthalate reaction product mixture obtained by reacting hydroxypropylmethyl cellulose, alkali acetate, phthalic anhydride and alkali chlorate in acetic acid solvent, wherein, after said reaction is completed, 2–4 wt. %, based on a 1 wt. % solution of hydroxypropylmethyl cellulose, of selected from the group consisting of a fluidization solvent water or $C_1$–$C_5$ low alcohol is added and stirred, and the product is sprayed into 10–20 wt. %, based on a 1 wt. % solution of hydroxypropylmethyl cellulose, of water through a spray nozzle whose air or nitrogen gas pressurization speed is 3–8 L/min, and then stirred, filtered and dried.

2. A purification method of hydroxypropylmethyl cellulose phthalate according to claim 1, wherein said hydroxypropylmethyl cellulose has a viscosity of 3–20 cps in 2% aqueous solution and includes less than 0.4% of chloride content.

3. A purification method of hydroxypropylmethyl cellulose phthalate according to claim 1, wherein said alkali acetate is sodium acetate or potassium acetate.

4. A purification method of hydroxypropylmethyl cellulose phthalate according to claim 1, wherein said alkali chlorate is sodium chlorate or potassium chlorate.

5. A purification method of hydroxypropylmethyl cellulose phthalate according to claim 1, wherein said fluidization solvent is water.

6. A purification method of hydroxypropylmethyl cellulose phthalate according to claim 1, wherein said $C_1$–$C_5$ low alcohol is methanol or ethanol.

7. A purification method of hydroxypropylmethyl cellulose phthalate according to claim 1, wherein the internal diameter of said spray nozzle is 0.5–1.5 mm.

8. A purification method of hydroxypropylmethyl cellulose phthalate according to claim 1, wherein the particle size of purified hydroxypropylmethyl cellulose phthalate is 50–300 meshes, corresponding to 300–50 μm.

* * * * *